United States Patent [19]

Todd et al.

[11] Patent Number: 5,084,031
[45] Date of Patent: Jan. 28, 1992

[54] CARDIOPLEGIA THREE-WAY DOUBLE STOPCOCK

[75] Inventors: Robert J. Todd, Salt Lake City; Douglas L. Smith, Murray; Michael N. Kelly, Salt Lake City, all of Utah

[73] Assignee: Research Medical, Inc., Midvale, Utah

[21] Appl. No.: 406,382

[22] Filed: Sep. 12, 1989

[51] Int. Cl.⁵ .............................................. A61M 5/00
[52] U.S. Cl. ..................................... 604/248; 137/595; 137/625.91; 137/625.47
[58] Field of Search .................... 604/32, 246, 248; 251/309; 137/595, 625.19, 625.23, 625.47, 626, 862

[56] References Cited

U.S. PATENT DOCUMENTS

| | | | |
|---|---|---|---|
| 246,538 | 8/1881 | Mullaney | 137/595 |
| 383,356 | 5/1888 | Hawkridge | 137/625.19 |
| 566,025 | 8/1896 | Schutte et al. | 137/625.47 |
| 1,270,722 | 6/1918 | Gillette | 137/595 |
| 2,538,215 | 1/1951 | Stack . | |
| 2,669,233 | 2/1954 | Friend . | |
| 2,833,151 | 5/1958 | Harvey | 137/625.47 |
| 3,098,506 | 7/1963 | Spragens | 137/625.19 |
| 3,499,467 | 3/1970 | McCord et al. | 137/625.19 |
| 3,678,959 | 7/1972 | Liposky | 137/625.11 |
| 3,834,372 | 9/1974 | Turney | 604/248 |
| 3,859,985 | 1/1975 | Eckhart | 128/2.05 R |
| 4,249,923 | 2/1981 | Walda | 62/394 |
| 4,355,659 | 10/1982 | Kelchner | 137/625.19 |
| 4,397,335 | 8/1983 | Doblar et al. | 137/625.19 |
| 4,416,280 | 11/1983 | Carpenter et al. | 128/399 |
| 4,427,009 | 1/1984 | Wells et al. | 128/400 |
| 4,433,971 | 2/1984 | Lindsay et al. | 604/122 |
| 4,459,977 | 7/1984 | Pizon et al. . | |
| 4,512,163 | 4/1985 | Wells et al. | 62/394 |
| 4,529,397 | 7/1985 | Hennemuth et al. | 604/4 |
| 4,566,480 | 1/1986 | Parham | 137/271 |
| 4,568,330 | 2/1986 | Kujawski et al. | 604/53 |
| 4,610,661 | 9/1986 | Possis et al. | 604/52 |
| 4,668,215 | 5/1987 | Allgood | 604/30 |
| 4,689,041 | 8/1987 | Corday et al. | 604/53 |
| 4,714,460 | 12/1987 | Calderon | 604/28 |
| 4,753,637 | 6/1988 | Horneffer | 604/53 |
| 4,804,358 | 2/1989 | Karcher et al. | 600/17 |
| 4,880,032 | 11/1989 | Doutt | 137/595 |

FOREIGN PATENT DOCUMENTS 0249338 12/1987 European Pat. Off. .

OTHER PUBLICATIONS

D. Glenn Pennington, "Direct Coronary Ostial Perfusion", Myocardial Protection in Cardiac Surgery, Chapter 14, edited by Arthur J. Roberts, published by Marcel Dekker Inc., pp. 229-250, (1987).

(List continued on next page.)

Primary Examiner—Stephen C. Pellegrino
Assistant Examiner—Ralph A. Lewis
Attorney, Agent, or Firm—Workman, Nydegger & Jensen

[57] ABSTRACT

A three-way double stopcock and associated tubing is disclosed with which to connect both a cardioplegia solution source and a pressure monitor for the solution selectively and alternatively to either an antegrade cardioplegia catheter or a retrograde cardioplegia catheter. The stopcock includes a hollow valve body with three solution infusion ports communicating to the interior thereof in a coplanar arrangement at a first longitudinal point on the valve body. Three cardioplegia pressure monitoring ports also communicate through the valve body to the interior thereof at a second longitudinal position distinct from the first. Mounted in the valve body is a cylindrical valve core selectively rotatable about the longitudinal axis thereof between a first position in which the cardioplegia solution source and the pressure monitor are coupled to the antegrade cannula and a second position in which the cardioplegia solution source and the pressure monitor are coupled to the retrograde catheter. Formed in the valve core are a set of valving passageways for communicating with selective of the infusion ports and a set of valving passageways for communicating with selective of the pressure monitoring ports.

42 Claims, 3 Drawing Sheets

John W. Kirklin, M. D., et al., "Prevention of Myocardial Damage During Cardiac Operations", *The New England Journal of Medicine*, vol. 301, No. 3, pp. 135-141, Jul. 19, 1979.

International Working Group on Coronary Sinus Interventions, Newsletter, vol. 1, No. 3, Oct., 1987.

Harold V. Liddle and Richard Berryessa, "Metabolic Management of the Myocardium during Cardiac Surgery," Blades Surgical Diseases of the Chest, Chapter 23, pp. 649-671, (1978).

Charles C. Reed, Diane K. Clark, "Cannulation" Chapter 19, Myocardial Protection Chapter 23, *Cardiopulmonary Perfusion*, Texas Medical Press, Inc., Houston, Tex. 1975.

Dr. Dwight C. McGoon, "Coronary Perfusion", *Journal of Thoracic and Cardiovascular Surgery*, vol. 70, No. 6, p. 1025, Dec. 1975.

Donald G. Mulder et al., "Myocardial Protection During Aortic Valve Replacement", *The Annals of Thoracic Surgery*, vol. 21, No. 2, Feb. 1976, pp. 123-130.

Jorge Solorzano, M. D. et al., "Retrograde Coronary Sinus Perfusion for Myocardial Protection During Cardiopulmonary Bypass", *The Annals of Thoracic Surgery*, vol. 25, No. 3, Mar. 1978, pp. 201-208.

Philippe Menasche et al., "Retrograde Coronary Sinus Perfusion", Roberts Textbook *Myocardial Protection in Cardiac Surgery*, printed 1987, Chapter 15, pp. 251-262.

Philippe Menasche, M. D. et al., "Retrograde Coronary Sinus Perfusion: A Safe Alternative for Ensuring Cardioplegic Delivery in Aortic Valve Surgery", *The Annals of Thoracic Surgery*, vol. 34, No. 6, Dec. 1982, pp. 647-658.

Gerald D. Buckberg, M. D., "Strategies and Logic of Cardioplegic Delivery to Prevent, Avoid, and Reverse Ischemic and Reperfusion Damage", *The Journal of Thoracic and Cardiovascular Surgery*, 1987, vol. 93, pp. 127-139, Gerald D. Buckberg, M. D., "Retrograde Pulmonary Venous Pressure Measurement—Fact or Artifact?", No. 3, pp. 393-406, Mar. 1970.

CARDIOPLEGIA THREE-WAY DOUBLE STOPCOCK

BACKGROUND

1. Field of the Invention

The present invention relates to methods and apparatus for controlling the flow and the monitoring the pressure of an infusion solution during cardioplegia procedures. More particularly, the present invention relates to a stopcock for effecting such functions where retrograde and antegrade cardioplegia procedures are being performed sequentially in the same surgery.

2. Background Art

It is recognized in cardiac surgery that the myocardial necrosis that occurs during surgery is due to the isolation of the heart from its life-giving blood supply. To reduce this damage to heart tissue it is known to infuse a cardioplegic solution into the blood vessels through which nutrients would normally reach the tissue of the heart. Cardioplegic solutions typically are cooled fluids containing potassium, magnesium procaine, or a hypocalcemic composition. The solutions still the heart and suppress tissue metabolism thermally and chemically.

Cardioplegia may be administered in an antegrade manner through coronary arteries in the normal direction of blood flow, or in a retrograde manner through coronary veins in a direction opposite to normal blood flow. In both procedures, before cardioplegia equipment is located in the heart, the heart is cannulated to create a cardiopulmonary bypass about the heart through a life-support system. That system typically includes an oxygenator, a pump, a blood filter, and a cardiotomy reservoir. Cannulation is effected using one or more venous return catheters and an aortic arch cannula. Suitable clamping is effected of the blood vessels involved so as to isolate the heart from blood flow.

In antegrade cardioplegia, a single cannula is inserted into the aortic root, and the cardioplegic solution is infused therethrough into the coronary arteries in the normal direction of blood flow. An antegrade cardioplegia cannula suitable for this purpose is disclosed in a copending U.S. Pat. application filed concurrently herewith and entitled "Antegrade Cardioplegia Cannula" which is incorporated herein by reference.

To enable a flow through of the cardioplegic solution, antegrade cardioplegia procedures are vented on the right side of the heart. This can be accomplished utilizing either a separate right ventricle vent, or a vent built into one of the other catheters located there. These might include the one or more of the venous return catheters utilized to bypass the heart to the life support system, or, if both types of cardioplegia procedure are being used in the same operation, the catheter used for retrograde cardioplegia. As the left side of the heart is normally exposed to relatively high fluid pressures, it has not routinely been the case that the pressure of cardioplegia solution in the heart in an antegrade cardioplegia procedure is consistently monitored.

In retrograde cardioplegia a balloon catheter is inserted through the right atrium into the coronary sinus. Inflation of the balloon stops the fluid flow from the tip of the catheter into the right atrium. The cardioplegic solution is administered through the catheter into the heart through the coronary veins branching from the coronary sinus in a direction reversed to that of normal blood flow. A suitable retrograde cardioplegia catheter for this purpose is disclosed in copending U.S. Pat. application Ser. No. 187,230, filed Apr. 28, 1988 and entitled "Retrograde Venous Cardioplegia Catheters and Methods For Use And Manufacture".

To enable a flow through of cardioplegic solution, in retrograde cardioplegia procedures the left side of the heart is vented, either using a separate left ventricular vent or by way of a vent built into other catheters or cannulas being used on that side of the heart. These might include the aortic arch cannula or, if both retrograde and antegrade cardioplegia are being employed in the same operation, the antegrade cardioplegia cannula. As the venous structures on the left side of the heart are not routinely subjected to high-fluid pressures, the monitoring of the cardioplegic solution in the heart at this point is essential and always undertaken.

While retrograde and antegrade cardioplegia each have particular strengths and weaknesses, if coronary artery blockage is major, the use of both procedures individually in sequence is necessitated, if heart tissues on the downstream sides of the arterial blockages is to be perfused by the cardioplegic solution and thus fully protected from myocardial necrosis.

Typically, when both procedures are to be employed, a single source of cardioplegic solution is Y-connected to the retrograde catheter and to the antegrade cannula. A clamp in each leg of the Y-connection permits the solution source to be connected to each selectively. To simplify matters, a single pressure monitor is employed and the fluid pressure on the left, arterial, or antegrade side is quite often simply not monitored at all. If fluid pressure on both sides is to be monitored, two monitors are used or a Y-connection similar to that used with a single source of cardioplegic solution is employed.

Where antegrade and retrograde cardioplegia procedures are utilized in sequence, the change from one to the other can be a cumbersome, time-consuming, and risk-filled undertaking. It is necessary upon switching from one procedure to the other to cut off fluid communication in the infusion tubing and in infused and then to open the corresponding tubing to the other side of the heart.

While the time in which to do so is of some concern, the major problem with this process is the break it causes in the concentration of the surgeon. In addition, the switchover is dangerous. For example, the failure to close one infusion tubing before opening the other could lead to infusion occurring at both sides of the heart, which can literally blow up the delicate blood supply tissues thereof. Another risk is that the pressure monitor will somehow become coupled to the side of the heart not being infused. Particularly where infusion is occurring on the right, venous, or retrograde side, this is a danger, as the failure to detect high pressures on the right side of the heart can result in edema or in tissue tearing in the venous structure of the heart.

These complications have led many surgeons to forego the use or the option to use both retrograde and antegrade cardioplegia in a single surgery. Thus, the maximum known protection from myocardial necrosis is not utilized and the methods and apparatus available in the art of cardiac surgery must regretfully be assessed as not keeping current.

BRIEF SUMMARY AND OBJECTS OF THE INVENTION

A major object of the present invention is to improve the effectiveness of cardiac surgery.

In this regard, it is a more specific object of the present invention to reduce myocardial necrosis occurring during cardiac surgery, both by contributing to more effective cardioplegia procedures, and by reducing the delays in surgical activities caused by same.

It is yet another object of the present invention to facilitate the use of alternate, sequenced retrograde and antegrade cardioplegia procedures during a single surgery.

Another object of the present invention is a method and apparatus that enables the use of a single source of cardioplegia fluid and a single pressure monitor when both retrograde and antegrade cardioplegia procedures are used in an alternating sequence in a single surgery.

Yet another object of the present invention is a method and apparatus as described above which simplifies the task of switching between retrograde cardioplegia and antegrade cardioplegia procedures and which reduces the opportunity for errors in doing so.

Yet another object of the present invention is to reduce the time required to switch between retrograde cardioplegia to antegrade cardioplegia procedures, when both are employed in alternating sequence in a given surgery.

Another object of the present invention is to facilitate pressure monitoring of cardioplegic procedures on both sides of the heart. An additional object of the present invention is to render more attractive to surgical practitioners the employment of the full range of cardioplegic procedures.

Additional objects and advantages of the invention will be set forth in the description which follows, and in part will be obvious from the description or may be learned by the practice of the invention. The object and advantages of the invention may be realized and obtained by means of the instruments and combinations particularly pointed out in the appended claims.

To achieve the foregoing objects and in accordance with the invention as embodied and broadly described herein, a cardioplegia stopcock is disclosed for use selectively both in an antegrade cardioplegia procedure and in a retrograde cardioplegia procedure to infuse solution and to monitor the pressure of the solution. The stopcock comprises a hollow valve body. Three cardioplegia solution infusion ports communicate through the walls of the valve body to the interior thereof, while three cardioplegia pressure monitoring ports similarly communicate through the walls of the valve body.

Fluid communication control means are provided for simultaneously regulating fluid communication among the infusion ports and among the pressure monitoring ports. The fluid communication control means is selectively operable between a first and a second condition. In the first condition a first and a second of the infusion ports are placed in fluid communication, while a first and a second of the pressure monitoring ports are simultaneously also placed and a third of the infusion ports are placed in fluid communication, while the second and a third of the pressure monitoring ports are simultaneously also placed in fluid communication.

Thus, the second infusion port and the second pressure monitoring port are in fluid communication through the stopcock in both conditions of the fluid communication control means. The second infusion port is connected to a single source of cardioplegia solution, while the second pressure monitoring port is connected to the single pressure monitor utilized. The first infusion port and the first pressure monitor port are connected respectively to the retrograde catheter and to the pressure sensing feed line associated therewith. Accordingly, when the fluid communication control means is in the first operative condition, the single cardioplegia solution source and the single pressure monitor are in fluid communication with that catheter. The third infusion port and the third pressure monitoring port coupled respectively to the antegrade cannula and to the associated pressure sensing feed line. Accordingly, when the fluid communication control means is in the second condition thereof, this cannula is coupled to the cardioplegia solution source and the pressure monitor.

Thus, the operation of a single stopcock of the present invention between the first and second conditions thereof promptly effects in a single action switching between retrograde and antegrade cardioplegia procedures.

In one embodiment of the present invention, the fluid communication control means takes the form of a cylindrical valve core mounted in the valve body for rotation about the longitudinal axis of the valve core between a first and a second position that correspond respectively to the first and second conditions of the fluid communication control means. Formed in the cylindrical core is a first set of valving passageways for communicating with selective of the infusion ports and a second set of valving passageways for communicating with selective of the pressure monitoring ports. In each instance, the valving passageways comprise a first bore diametrically disposed through the cylindrical core and a second bore radially disposed normal to and communicating with the first bore.

Preferably the infusion ports are radially disposed in a coplanar configuration at a first longitudinal position on the valve body, while the pressure monitoring ports are radially disposed in a coplanar configuration at a second longitudinal position on the valve body distinct from the first longitudinal position.

Conventionally, the diameter of the pressure monitoring ports is substantially smaller than the diameter of the infusion ports. Appropriately sized pressure monitoring and infusion tubing is permanently secured to the various ports of the stopcock and provided at the ends remote therefrom with suitable connectors for effecting fluid tight seals with the other apparatus utilized in the procedures involved.

In one presently preferred embodiment of the present invention, the cylindrical valve core itself comprises a first valve core subassembly having formed therein a first set of valving passageways and a second valve core assembly in which is formed the second set of valving passageways. The second valve core subassembly is mounted in the valve body coaxially with the first valve subassembly at a first end thereof. A tie bar rigidly secured to the first end of the first core subassembly and the end of the second core subassembly opposite thereto causes the two subassemblies to rotate together. This rotation may be affected by an activation lever secured to either end of the composite valve core.

In addition, the valve body of the inventive stopcock can itself comprise a first cylindrical shell having formed therethrough infusion ports and a second cylindrical shell disposed coaxially with said first cylindrical shell at a first end thereof and having formed therethrough the pressure monitoring ports. A sleeve encircling the first end of the cylindrical shell and the end of the second cylindrical shell opposed thereto maintains a fixed spacial relationship between the two components of the composite valve body.

The resultant stopcock permits easy switching from retrograde to antegrade cardioplegia procedures, eliminating the risks resulting from error in the sequencing of tube closures and openings during such switchovers. When used in conjunction with attached infusion and pressure monitoring tubing, the inventive stopcock functions therewith as a system for interconnecting the catheter, cannula, pressure monitor, and fluid source used for selectively conducting retrograde and antegrade cardioplegia procedures in a single operation.

BRIEF DESCRIPTION OF THE DRAWINGS

In order that the manner in which the above-recited and other advantages and objects of the invention are obtained, a more particular description of the invention briefly described above will be rendered by reference to the specific embodiments thereof which are illustrated in the appended drawings Understanding that there drawings depict only typical embodiments of the invention and are therefore not to be considered limiting of its scope, the invention will be described with additional specificity through the use of the accompanying drawings in which.

DETAILED DESCRIPTION OF THE PREFERRED EMBODIMENTS

Figure 1:
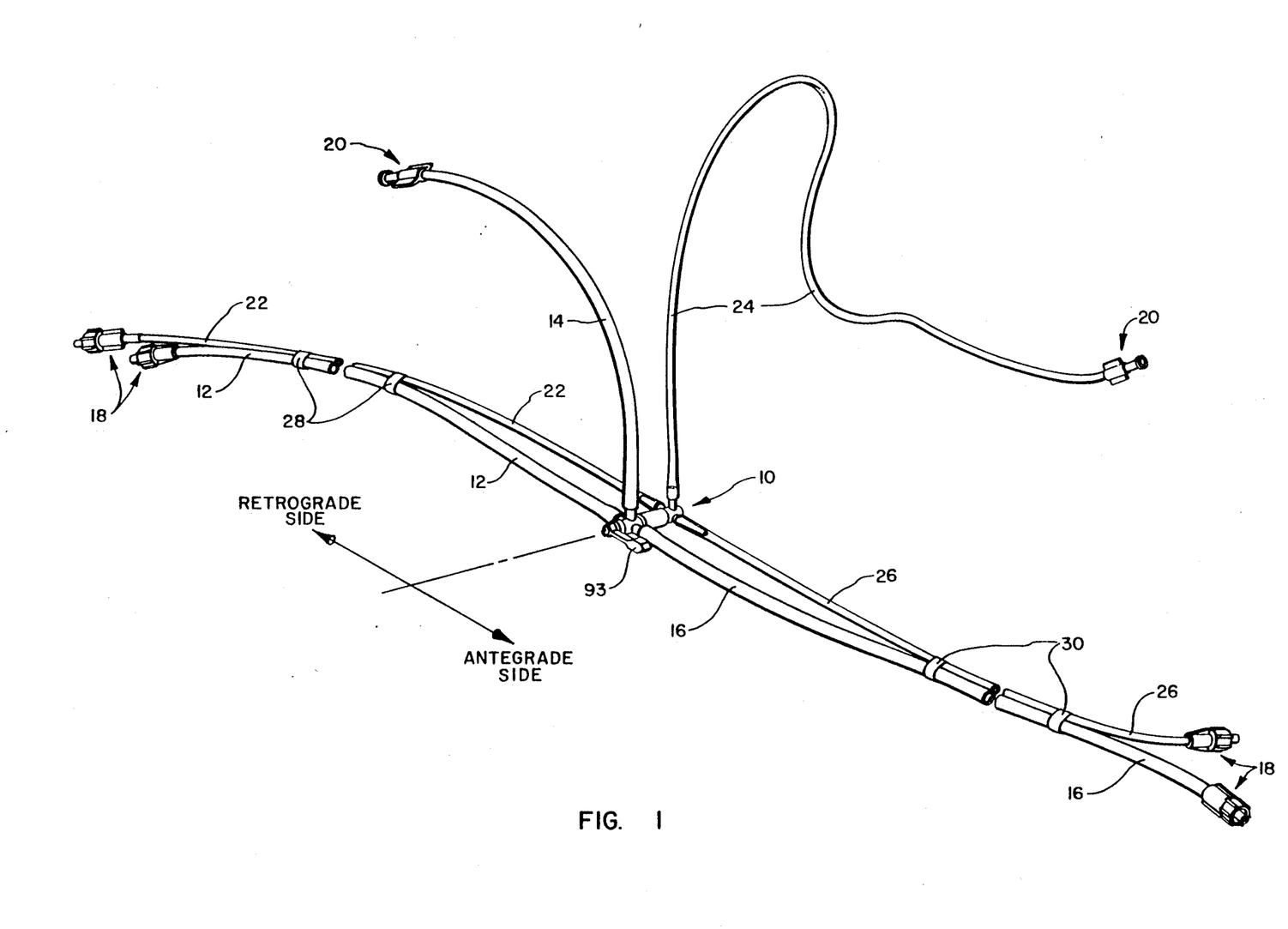
FIG. 1 is a perspective view of a three-way double stopcock and attached infusion and pressure monitoring tubing incorporating teachings of the present invention.

In the drawings and in the discussion to follow, like parts will be designated with like reference characters throughout. Referring first to FIG. 1, one presently preferred embodiment of a three-way double stopcock 10 is shown with associated tubing attached thereto. The components shown together function as a system for interconnecting both a source of cardioplegia solution and a pressure monitor for a cardioplegia procedure selectively and alternately to an antegrade cardioplegia catheter having a pressure sensing feedline and a retrograde cardioplegia catheter having a pressure sensing feedline.

Among the tubing preferably permanently secured to stopcock 10 are first, second, and third infusion tubing 12, 14, 16, respectively. The ends of infusion tubing 12, 14, 16 remote from stopcock 10 are provided with fittings for effecting fluid-tight couplings to other cardioplegia equipment. Thus, as shown by way of example in FIG. 1, the free ends of first and third infusion tubing 12, 16 remote from stopcock 10 are provided with male luer connectors 18, while the end of second infusion tubing 14 remote from stopcock 10 is provided with a female luer connector 20.

Also associated with stopcock 10 are first, second, and third pressure tubing 22, 24, 26. Pressure tubing 22, 24, 26 are similarly provided at the ends thereof remote from stopcock 10 with fittings, such as a male luer connector 18 shown at the ends of first and third pressure tubing 22, 26, respectively, or a female luer connector 20 at the extreme end of second pressure tubing 24. These fittings also are used to effect fluid-tight couplings between pressure tubing 22, 24, 26 and other cardioplegia pressure monitoring equipment.

In the system illustrated in FIG. 1, second infusion tubing 14 is intended to be coupled to a source of cardioplegia solution for infusion into a patient, preferably alternately in antegrade and in retrograde procedures. Second pressure tubing 24 is correspondingly intended to be coupled to a pressure monitor through which to register the pressure of the cardioplegia solution in the patient in each alternate procedure. First infusion tubing 12 and first pressure tubing 22 are to be coupled to a retrograde catheter and its associated pressure sensing feedline. Third infusion tubing 16 and third pressure tubing 26 are to be coupled to a cannula and its associated pressure-sensing feedline.

This pairing of infusion tubing and pressure tubing permits each side of the system illustrated to be designated as either antegrade or retrograde. Accordingly, in FIG. 1 first infusion tubing 12 and first pressure tubing 22 have been designated as leaving stopcock 10 on the retrograde side thereof. Correspondingly, third infusion tubing 16 and third pressure tubing 26 are designated as leaving stopcock 10 on the antegrade side thereof. While this designation is to a degree arbitrary, it is preferred given the typical position of the equipment illustrated in FIG. 1 in relation to the patient, the cardiac surgeon, and the staff assistants thereof. Nevertheless, it should be understood that an embodiment of a stopcock, such as stopcock 10, is conceivable within the scope of the present invention in which such pairing might be reversed or not even affected at all. The employment of other principles of the present invention would nevertheless result in an apparatus yielding substantial, if not all, of the advantages of the embodiment shown in FIG. 1.

As both first infusion tubing 12 and first pressure tubing 22 are to be coupled to the same device, in this instance a retrograde catheter, first infusion tubing 12 and first pressure tubing 22 are tied to each other at one or more locations along the course thereof by tape 28. Typically the length of first infusion tubing 12 and first pressure tubing 22 would be in the range of about 10.0 inches to about 15.0 inches.

Similarly, third infusion tubing 16 and third pressure tubing 26, which are to be coupled to the same device, in this instance an antegrade cannula, are tied at one or more locations along the length thereof by tape 30. The length of third infusion tubing 16 and third pressure tubing 26 is in the range of about 4.0 inches to about 10.0 inches It is also contemplated that by adding about 60.0 inches to about 80.0 inches more to the length of each of first and third pressure tubing 22, 26 and first and third infusion tubing 12, 16, the control of switching between retrograde and antegrade cardioplegia procedures can be moved away from the immediate site of the surgery, so as to be conducted by a perfusionist outside of the immediate ring of the surgeon and the surgery staff. This would result in first infusion tubing 12 and first pressure tubing 22 having lengths in the range of about 70.0 inches to about 95.0 inches. Correspondingly, the lengths of third infusion tubing 16 and third pressure tubing 26 would be in the range of about 64.0 inches to about 90.0 inches.

Tapes 28, 30 can be color-coded to assist the user in appreciating an intended orientation of stopcock 10 and its associated tubing to the other apparatus utilized in the cardioplegia procedures. Thus, as the tubing on the antegrade side of stopcock 10 is to infuse and pressure monitor cardioplegia solution entering the arterial side of the blood vessels of the heart, tape 28 might be colored red. As the tubing on the retrograde side of stopcock 10 permits the infusion of cardioplegia solution into the venous side of the blood vessels, tape 30 could be made blue.

For convenience of operation, second infusion tubing 14 is provided with a length in the range of about 3.0 inches to about 8.0 inches, while second pressure tubing 24 can be afforded a longer length in the range of 60.0 inches to about 80.0 inches, which permits pressure monitoring equipment to be located remotely from the actual site of surgery.

Figure 2:
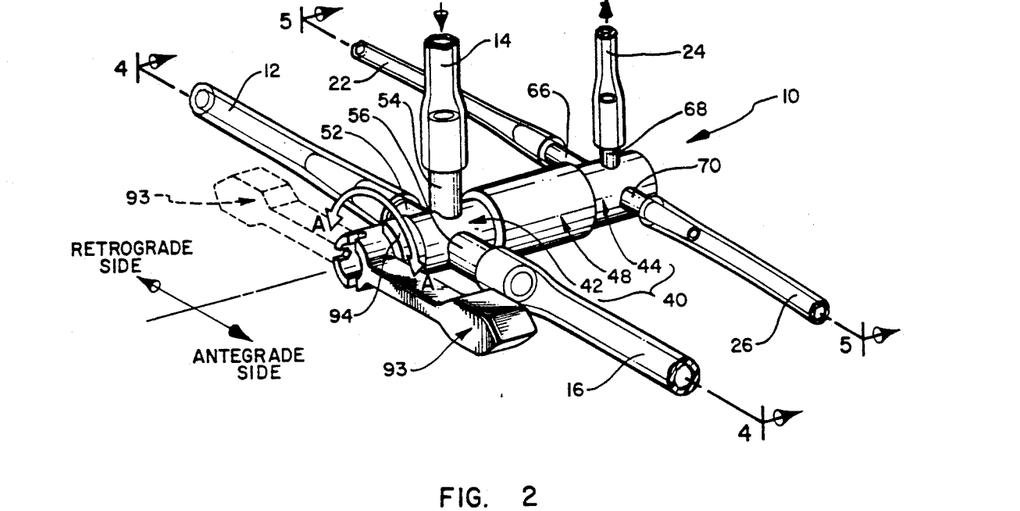
FIG. 2 is an enlarged detail perspective view of the stopcock shown in FIG. 1.
Figure 3:
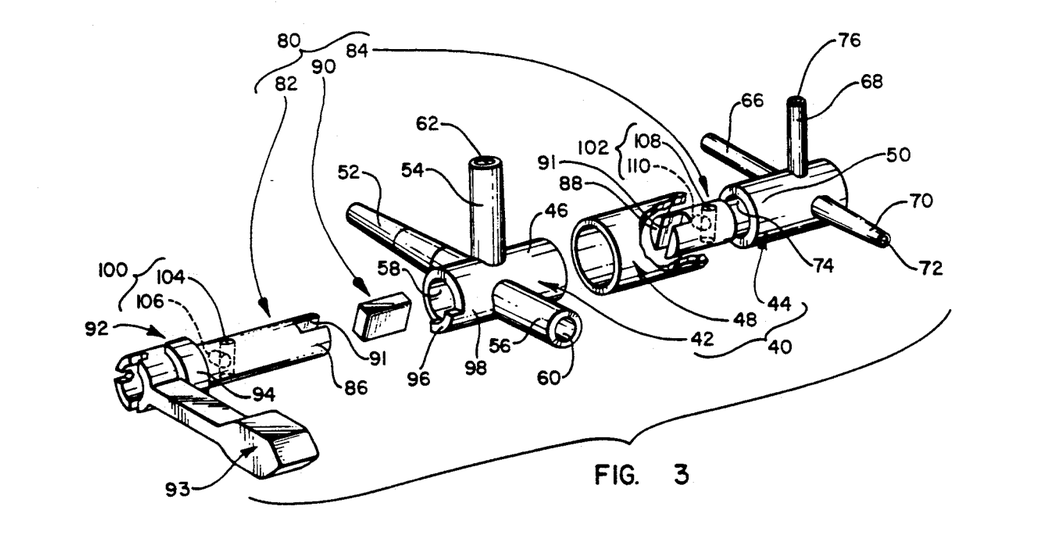
FIG. 3 is an exploded perspective view of the components of the stopcock shown in FIG. 2.

Stopcock 10 can be appreciated in greater detail and advantage by reference to FIGS. 2 and 3 taken together. There it can be seen that stopcock 10 includes a hollow valve body 40 which itself may comprise a first cylindrical shell 42 and a second cylindrical shell 44 disposed coaxially therewith at a first end 46 thereof. A sleeve 48 encircles first end 46 of first cylindrical shell 42 and the end 50 of second cylindrical shell 44 opposed thereto. In this manner sleeve 48 maintains a fixed spatial relationship between first and second cylindrical shells 42, 44, respectively.

From the exterior of first cylindrical shell 42 project first, second, and third infusion connection stems 52, 54, 56, respectively, which are disposed in a coplanar configuration at a first longitudinal position along valve body 40. First and third infusion connection stem 52, 56, respectively, are located on diametrically opposite sides of first cylindrical shell 42, while second infusion connection stem 54 is spaced at a right angle about first cylindrical shell 42 to both first and third infusion connection stems 52, 56, respectively.

Infusion connection stems 52, 54, 46 are tubular, defining therewithin a cardioplegia solution infusion port that communicates through the walls of first cylindrical shell 42 to the interior 58 thereof. Thus, third infusion port 60 communicates between the interior 58 and exterior of first cylindrical shell 42 through third infusion connection stem 56. Similarly, second infusion port 62 is within second infusion connection stem 52, and first infusion port 64 (shown only in figures subsequent to FIG. 3) is housed within first infusion connection stem 52.

Second cylindrical shell 44 is similarly configured. First, second, and third pressure monitoring connection stems 66, 68, 70, respectively, extend radially outwardly from the exterior of second cylindrical shell 44 in a coplanar manner at a longitudinal point along valve body 40 distinct from that at which infusion connection stems 52, 54, 56 are located. Within third pressure monitoring connection stem 70 is third pressure monitoring port 72 which communicates between the interior 74 and exterior of second cylindrical shell 44. Similarly, a second pressure monitoring port 76 is located at the center of second pressure monitoring connection stem 68 and a first pressure monitoring port 78 (shown only in figures subsequent to FIG. 3) communicates between the exterior and interior 74 of second cylindrical shell 44 through first pressure monitoring connection stem 66.

Infusion connection stems 52, 54, 56 and pressure monitoring stems 66, 68, 70 provide a structure by which the tubing associated with stopcock 10 may be secured thereto.

First and third pressure monitoring connection stems 66, 70 are located on diametrically opposite sides of second cylindrical shell 44 of valve body 40. Second pressure monitoring connection stem is spaced at a right angle about second cylindrical shell 44 to both first and third pressure monitoring connection stems 66, 70, respectively.

For optimum convenience, first infusion connection stem 52 and first pressure monitoring connection stem 66 are longitudinally aligned on the sides of valve body 40. Similarly, second infusion connection stem 54 and second pressure monitoring connection stem 68 are longitudinally aligned, but at right angles to first infusion connection stem 52 and first pressure monitoring connection stem 66. Finally, third infusion connection stem 56 and third pressure monitoring connection stem 70 are also longitudinally aligned on valve body 40 diametrically opposite first infusion connection stem 52 and first pressure monitoring connection stem 66, at a right angle to each of second infusion connection stem 54 and second pressure monitoring connection stem 68. Although this manner of physical layout need not be pursued in order to enjoy some advantages of the present invention, the arrangement shown does result in the clarified physical layout of stopcock 10 discussed in relation to FIG. 1. Accordingly, in FIG. 2 an antegrade side and a retrograde side of stopcock 10 is designated.

In one aspect of the present invention, fluid communication control means are provided for simultaneously regulating fluid communication among infusion ports 60, 62, 64 and among pressure monitoring ports 66, 68, 70. As shown by way of example and not limitation in FIG. 3, a cylindrical valve core 80 comprises a first valve core subassembly 82 and a second valve core subassembly 84 positioned coaxially therewith at a first end 86 thereof.

Valve core assemblies 82, 84 are mounted in valve body 40 for rotation therein about the longitudinal axis of valve core assemblies 82, 84. Valve core subassemblies 82, 84 are secured in a fixed spatial relationship so as to rotate together within valve body 42. This can be accomplished in any number of structural arrangements by which first end 86 of valve core 82 is secured to the end 88 of valve core subassembly 84 opposite thereto. By way of example and not limitation, FIG. 3 illustrates that a tie bar 90 is rigidly secured to first end 86 of first valve core subassembly 82 and to the end 88 of second valve core subassembly 84 opposite thereto. The opposite ends of tie bar 90 are received in slots 91 in first end 86 of first valve core subassembly 82 and in end 88 of second valve core subassembly 84. An adhesive may be used to assist in this regard. Alternatively, tie bar 90 may be provided with opposed sharpened ends which penetrate the material of valve core subassemblies 82, 84 when those two subassemblies are pressed together with tie bar 90 sandwiched therebetween.

One end 92 of first valve core subassembly 82 extends axially beyond valve body 40 and is provided thereat with an actuation lever 93 for rotating valve core 80. Actuation lever 93 is provided with a shoulder 94 which cooperates with a boss 96 on the end 98 of first valve core subassembly 82 opposite first end 86 thereof to restrict rotation of actuation lever 93 and valve core 80 attached thereto to the 180° of rotational motion indicated in FIG. 2 by arrow A.

Valve core 80 fits tightly within valve body 40 so as generally to block the inner end of infusion ports 60, 62, 64 and pressure monitoring ports 72, 76, 78. Nevertheless, valve core 80 is able to regulate fluid communication among infusion ports 60, 62, 64, while simultaneously regulating fluid communication among pressure monitoring ports 72, 76, 78. This is achieved using a first set 100 of valving passageways formed in first valve core subassembly 82 and a second set 102 of valving passageways formed in second valve core subassembly 84. First set 100 of valving passageways comprises a first bore 104 diametrically disposed through first valve core subassembly 82 and a second bore 106 disposed normal to and communicating with first bore 104. Similarly, second set of valve passageways 102 comprises a first bore 108 diametrically disposed through second valve core subassembly 84 and a second bore 110 disposed normal to and communicating with first bore 108. The orientation of actuation lever 93 is diametrically opposite to second bores 106, 110. Actuation lever 93 thus points in the direction of the infusion port and the pressure monitoring port that is not in fluid communication with any other.

Figure 4A:
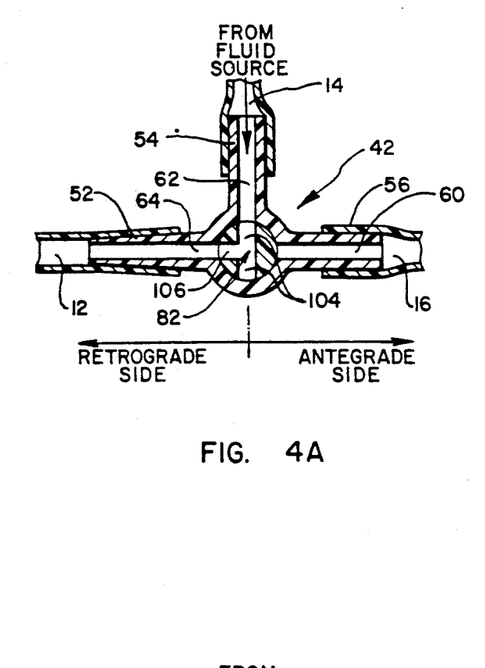
FIG. 4A is a cross-sectional view of the stopcock shown in FIG. 2 taken along section line 4—4 shown therein with the valve core and actuation lever thereof in the position shown in solid lines.
Figure 4B:
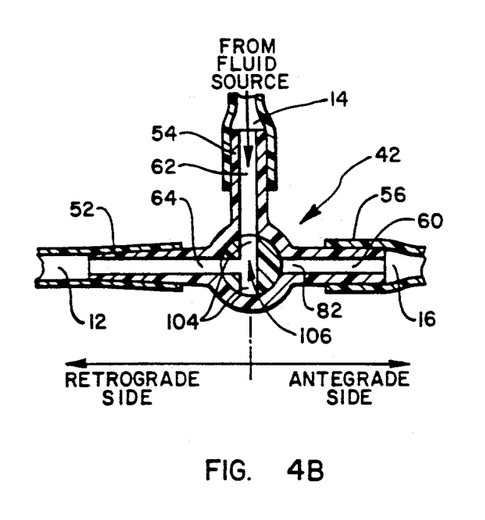
FIG. 4B is a cross-sectional view of the stopcock shown in FIG. 2 taken along section line 4—4 shown therein with the valve core and actuation lever thereof in the position shown in phantom lines.

Valve core 80 with actuation lever 93 attached thereto is operable between a first position at one extreme of arrow A shown in FIG. 2 in solid lines and a second position at the opposite extreme of arrow A shown in FIG. 2 in phantom. In the first position, which is reflected also in FIG. 3, first bore 104 communicates with second infusion port 62, while second bore 106 opens into first infusion port 64. Third infusion port 64 is blocked by first valve core subassembly 82. This situation is better illustrated in FIG. 4A. Accordingly, cardioplegic solution from second infusion tubing 14 will in the first position of valve core 80 be communicated to first infusion port 64 on the retrograde side of stopcock 10.

Figures 5A, 5B:
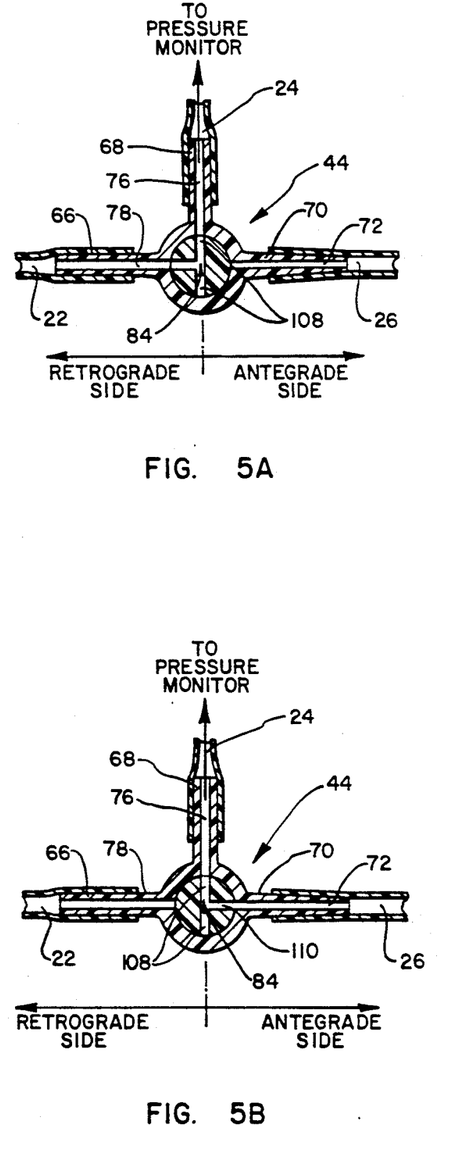
FIG. 5A is a cross-sectional view of the stopcock shown in FIG. 2 taken along section line 5—5 shown therein with the valve core and actuation lever thereof in the position shown in solid lines.
FIG. 5B is a cross-sectional view of the stopcock shown in FIG. 2 taken along section line 4B—4B shown therein with the valve core and actuation lever thereof in the position shown in phantom lines.

The relationship of the components of stopcock 20 at first, second, and third pressure monitoring ports 78, 76, and 72, respectively, in the first position of valve core 80 is shown in FIG. 5A. As seen there, first bore 108 opens onto second pressure monitoring port 76, while second bore 110 communicates with first pressure monitoring port 78. Third pressure monitoring port 72 is blocked by second valve core subassembly 84. Accordingly, the pressure in the antegrade cannula to which third pressure tubing 26 is coupled will be communicated through third pressure tubing 26 to second pressure tubing 24 and the pressure monitor employed during the cardioplegia procedure.

Rotation of actuator lever 93 out of the first position thereof shown in solid lines in FIG. 2 into the second position thereof shown in phantom lines in FIG. 2 alters this fluid communication, both in relation to the infusion ports and the pressure monitoring ports of stopcock 10. As shown in FIG. 5A, when actuator lever 93 and valve core 80 attached thereto are in the second position of valve core 80, first bore 104 communicates with second infusion port 62, but second bore 106 then opens into third infusion port 60. First infusion port 60 is blocked by first valve core subassembly 82. Accordingly, cardioplegic solution from second infusion tubing 14 will in the second position of valve core 80 be communicated to third infusion port 60 on the retrograde side of stopcock 10.

Simultaneously, as shown in FIG. 5B, at the other end of stopcock 10, first bore 108 communicates with second pressure monitoring port 76, and second bore 110 opens into third pressure monitoring port 72. First pressure monitoring port 78 is blocked by second valve core subassembly 84. Under such circumstances, the pressure in the antegrade cannula at the site of cardioplegic infusion is communicated through third pressure tubing 26 to second pressure tubing 24 and to the pressure monitor employed.

In this manner actuation of but a single valve is capable of effecting all changes in fluid communication required to switch between an antegrade and a retrograde cardioplegia procedure. The correct ordering of the closure and the opening of fluid lines is automatically insured. Risks are eliminated. The automatic monitoring of pressure in both procedures is insured. No uncoupling or additional opening or closing of tubing is required toward this end. Time and concentration are saved so that surgeons will be less resistant to the use of complete and complimentary cardioplegia involving both retrograde and antegrade procedures.

In one embodiment of a stopcock 10, first and second cylindrical shells 42, 44 are made of clear polycarbonate, while first and second valve core subassemblies 82, 84 can be made of opaque polyethylene. The diameter of infusion ports 60, 62, 64 in cylindrical shell 42 is about 0.90 inches, while that of pressure monitoring ports 72, 76, 78 associated with cylindrical shell 44 are smaller, being about 0.56 inches.

Tie bar 90 is metallic and can be of any suitable configuration, provided only that the lateral advancement of first and second valve core subassemblies 82, 84 toward each other causes tie bar 90 to penetrate or be bonded to both. Tie bar 90 can be advantageously be provided with lateral or diagonal fluting to effect a stronger securement to first and second valve core subassemblies 82, 84, respectively.

Sleeve 48 is an injection molded resin structure compatible with bonding to polycarbonates. It is secured about the abutting ends of first and second cylindrical shells 42, 44 using cyanoacrylate or other suitable bonding agents.

Tubing is attached to connection stems 52, 54, 56, 66, 68, and 70 in a conventional manner and made secure on a permanent basis, if desired, by the use of appropriate adhesives. Infusion tubing 12, 14, 16 has an inner diameter of about 0.135 inches, while pressure tubing 22, 24, 26 is provided with an inner diameter of about 0.050 inches.

The manner in which stopcock 10 is manufactured will be described briefly. Basically, the main elements of stopcock 10 are two stopcocks which are modified and joined to produce a device capable of single-action functioning as described above. While any number of known stopcocks could be used for this purpose, the embodiment of a stopcock 10 as described above was manufactured using a 0.90 inch through-diameter three-way stopcock marketed by Mallinckrodt Critical Care of Costa Mesa, Calif. under Product No. 30075 and a 0.56 inch through-diameter three-way stopcock marketed by the same company under Product No. 300173. Both stopcocks are supplied with actuation levers, such as actuation lever 93.

Initially, the actuation levers are aligned with the middle connection stem of each of the stopcocks. A tie bar is pressed into the end of the valve core of the larger through-diameter stopcock, opposite from the handle thereof. At least half of the length of the tie bar then protrudes from the valve core. Adhesive is not used in this process, but the tie bar is sized so as to fit snugly, without rotation into the hollow cavity the manufacture places in the end of the valve core opposite from the handle of the stopcock. The connection sleeve is then placed over the exterior of the valve body of the same stopcock. The fit should be snug.

Thereafter, with the actuation lever of the second, smaller through-diameter stopcock being remote from that of the first stopcock, the two are longitudinally aligned and pressed into engagement with each other. The protruding portion of the tie bar is thus forced into the opening at the center of the valve core of the second stopcock remote from the actuation lever thereof. At the same time, the valve body of the second stopcock passes inside the connection sleeve.

This assembly is baked for about one hour at about 150 degrees Fahrenheit to temper the constituent elements thereof and to equalize the stresses in the resulting structure. Cooling then occurs for at least 15 minutes. Then a single drop of cyanoacrylate or other suitable bonding agent is applied at each end of the connection sleeve and the resultant structure is allowed to dry for two hours.

Finally, the actuation lever of the second, small through-diameter stopcock is sheared off, the device is tested to verify its operation, and the tubing illustrated in FIG. 1 with associated connection fittings are attached.

In the alternative, stopcock 10 can be manufactured using a valve body 40 that is integrally molded as a single piece of clear polycarbonate, rather than comprising two separate cylindrical shells as described above. Similarly, valve core 80 can be fabricated as an integrally molded, opaque polyethylene structure, rather than being comprised of a plurality of valve core subassemblies. The unitary valve body operative stopcock.

In use, following heart cannulation as already described and the following installation of an antegrade cardioplegia cannula in the aortic route and a retrograde cardioplegia catheter in the coronary sinus, the tubing associated with stopcock 10 illustrated in FIG. 1 is attached and the system is purged with solution. Cardioplegia is then administered for one to two minutes in, for example, an antegrade procedure. Then, by switching the position of the actuation lever of stopcock 10, this is followed by one to two minutes, for example, of retrograde cardioplegia procedure. Surgery is undertaken until the cardioplegia procedures require repetition. This continues until surgery is finished.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A three-way double stopcock comprising:
   (a) a hollow valve body comprising:
      (i) a first cylindrical shell;
      (ii) a second cylindrical shell disposed coaxially with said first cylindrical shell at a first end thereof; and
      (iii) a sleeve encircling said first end of said first cylindrical shell and the end of said second cylindrical shell opposed thereto to maintain a fixed spacial relationship between said first and said second cylindrical shells;
   (b) a first set of three fluid ports formed through the walls of said first cylindrical shell communicating with the interior thereof;
   (c) a second set of three fluid ports formed through the walls of said second cylindrical shell communicating with the interior thereof; and
   (d) fluid communication control means for simultaneously regulating fluid communication among said first set of fluid ports and among said second set of fluid ports.

2. A three-way double stopcock as recited in claim 1, wherein said fluid communication control means simultaneously limits fluid communication among said fluid ports to fluid communication between either of two predetermined pairs of fluid ports within each of said first and second sets thereof.

3. A three-way double stopcock as recited in claim 1, wherein said fluid communication control means is selectively operable between a first condition in which a first and a second fluid port are placed in fluid communication in each of said first and second sets of fluid ports, and a second condition in which said second and a third fluid port are placed in fluid communication in each of said first and second sets of fluid ports.

4. A three-way double stopcock as recited in claim 3, further comprising an actuation means for operating said fluid communication control means between said first and second positions thereof.

5. A three-way double stopcock as recited in claim 3, wherein said fluid communication control means comprises a cylindrical valve core mounted in said valve body for rotation about the longitudinal axis of said value core between a first position and a second position thereof corresponding respectively to said first and second conditions of said fluid communication control means.

6. A three-way double stopcock as recited in claim 5, wherein one end of said cylindrical core extends axially actuation lever for rotating said cylindrical core.

7. A three-way double stopcock as recited in claim 5, wherein formed in said cylindrical core is a first set of valving passageways for communicating with selective of said first set of fluid ports.

8. A three-way double stopcock as recited in claim 7, wherein said first set of valving passageways comprises:
   (a) a first bore diametrically disposed through said cylindrical core; and
   (b) a second bore radially disposed normal to and communicating with said first bore.

9. A three-way double stopcock as recited in claim 5, wherein formed in said cylindrical core is a second set of valving passageways for communicating with selective of said second set of fluid ports.

10. A three-way double stopcock as recited in claim 9, wherein said second set of valving passageways comprises:
    (a) a first bore diametrically disposed through said cylindrical core; and
    (b) a second bore radially disposed normal to and communicating with said first bore.

11. A three-way double stopcock as recited in claim 1, wherein said fluid communication control means comprises:
    (a) a first cylindrical core mounted in said first cylindrical shell for rotation about the longitudinal axis thereof, said first cylindrical core having formed therein a first set of valving passageways for communicating with selective of said first set of fluid ports;
    (b) a second cylindrical core mounted in said second cylindrical shell coaxially with said first cylindrical core at a first end thereof for rotation about the longitudinal axis of said valve body, said second cylindrical core having formed therein a second set of valving passageways for communicating with selective of said second set of fluid ports; and
    (c) a tie bar rigidly secured to a first end of said first cylindrical core and to the end of said second cylindrical core opposite thereto to cause said first and said second cylindrical cores to rotate together.

12. A three-way double stopcock as recited in claim 1, wherein said first set of fluid ports is radially disposed in a coplanar configuration on said first cylindrical shell, and wherein said second set of fluid ports is radially disposed in a coplanar configuration on said second cylindrical shell.

13. A three-way double stopcock as recited in claim 1, wherein the diameter of said second set of fluid ports is substantially smaller than the diameter of said first set of fluid ports.

14. A cardioplegia stopcock for use alternately and selectively in an antegrade cardioplegia procedure and in a retrograde cardioplegia procedure to infuse and to pressure monitor in those procedures, the stopcock comprising:
    (a) a hollow valve body comprising:
        (i) a first cylindrical shell;
        (ii) a second cylindrical shell disposed coaxially with said first cylindrical shell at a first end thereof; and
        (iii) a sleeve encircling said first end of said first cylindrical shell and the end of said second cylindrical shell opposed thereto to maintain a fixed spacial relationship between said first and second shells;
    (b) three cardioplegia solution infusion ports communicating through the walls of said first cylindrical shell to the interior thereof;
    (c) three cardioplegia pressure monitoring ports communicating through the walls of said second cylindrical shell to the interior thereof; and
    (d) fluid communication control means for simultaneously regulating fluid communication among said infusion ports and among said pressure monitoring ports.

15. A three-way double stopcock comprising:
    (a) a hollow valve body comprising:
        (i) a first cylindrical shell;
        (ii) a second cylindrical shell disposed coaxially with said first cylindrical shell at a first end thereof; and
        (iii) a sleeve encircling said first end of said first cylindrical shell and the end of said second cylindrical shell opposed thereto to maintain a fixed spacial relationship between said first and said second cylindrical shells;
    (b) a first set of three fluid ports communicating through the walls of said first cylindrical shell to the interior thereof;
    (c) a second set of three fluid ports communicating through the walls of said second cylindrical shell to the interior thereof, the diameter of said second set of fluid ports being substantially smaller than the diameter of said first set of fluid ports; and
    (d) a cylindrical valve core mounted in said valve body for selective rotation about the longitudinal axis thereof between a first position in which a first and a second fluid port are placed in fluid communication in each of said first and second sets of fluid ports and a second position in which said second and a third fluid port are placed in fluid communication in each of said first and second sets of fluid ports.

16. A three-way double stopcock as recited in claim 15, wherein formed in said cylindrical core is a first set of valving passageways for communicating with selective of said first set of fluid ports.

17. A three-way double stopcock as recited in claim 16, wherein said first set of valving passageways comprises:
    (a) a first bore diametrically disposed through said cylindrical core; and
    (b) a second bore radially disposed normal to and communicating with said first bore.

18. A three-way double stopcock as recited in claim 15, wherein formed in said cylindrical core is a second set of valving passageways for communicating with selective of said second set of fluid ports.

19. A three-way double stopcock as recited in claim 18, wherein said second set of valving passageways comprises:
    (a) a first bore diametrically disposed through said cylindrical core; and
    (b) a second bore radially disposed normal to and communicating with said first bore.

20. A three-way double stopcock as recited in claim 15, wherein said first set of fluid ports is radially disposed in a coplanar configuration on said first cylindrical shell, and wherein said second set of fluid ports is radially disposed in a coplanar configuration on said second cylindrical shell.

21. A three-way double stopcock as recited in claim 20, wherein said first, second, and third fluid ports in said first set of fluid ports communicate with the exterior of said valve body through radially extending first, second, and third connection stems, respectively 22. A three-way double stopcock as recited in claim 21, wherein said first, second, and third fluid ports in said second set of fluid ports communicate with the exterior of said valve body through radially extending first, second, and third connection stems, respectively.

23. A three-way double stopcock as recited in claim 22, wherein said first and third connection stems are located on diametrically opposite sides of said valve body, and said second connection stem is spaced at right angles about said valve body from said first and said third connection stems.

24. A three-way double stopcock as recited in claim 23, wherein said first and third connection stems are located on diametrically opposite sides of said valve body, and said second connection stem is spaced at right angles about said valve body from said first and said third connection stems.

25. A three-way double stopcock as recited in claim 24, wherein said first, second, and third connection stems are longitudinally aligned respectively on the sides of said valve body.

26. A three-way double stopcock as recited in claim 25, wherein said cylindrical valve core comprises:

(a) a first valve core subassembly mounted in said valve body for rotation about the longitudinal axis thereof, said first valve core subassembly having formed therein a first set of valving passageways for communicating with selective of said first set of fluid ports;

(b) a second valve core subassembly mounted coaxially with said valve body at a first end thereof for rotation about the longitudinal axis of said valve body, said second valve core subassembly having formed therein a second set of valving passageways for communicating with selective of said second set of fluid ports; and (c) a tie bar rigidly secured to said first end of said first cylindrical core and to the end of said second cylindrical core opposite thereto to cause said first and said second cylindrical cores to rotate together.

27. A three-way double stopcock as recited in claim 15, wherein one end of said cylindrical core extends axially beyond said valve body, and said one end is provided with an actuation lever for rotating said cylindrical core.

28. A cardioplegia stopcock for use alternately and selectively in an antegrade cardioplegia procedure and in a retrograde cardioplegia procedure to infuse and to pressure monitor in those procedures, the stopcock comprising:

(a) a hollow valve body comprising:
 (i) a first cylindrical shell;
 (ii) a second cylindrical shell disposed coaxially with said first cylindrical shell at a first end thereof; and
 (iii) a sleeve encircling said first end of said first cylindrical shell and the end of said second cylindrical shell opposed thereto to maintain a fixed spacial relationship between said first and second shells;

(b) three cardioplegia solution infusion ports communicating through the walls of said first cylindrical shell to the interior thereof;

(c) three cardioplegia pressure monitoring ports communicating through the walls of said second cylindrical shell to the interior thereof; and (d) a cylindrical valve core mounted in said valve body for selective rotation about the longitudinal axis thereof between a first position in which a first and a second of said infusion ports and a first and a second of said pressure monitoring ports are placed in fluid communication, and a second position in which said second and a third of said infusion ports and said second and a third of said pressure monitoring ports are placed in fluid communication.

29. A system for interconnecting both a source of cardioplegia solution and a pressure monitor for cardioplegia procedures selectively and alternately to an antegrade cardioplegia cannula having a pressure sensing feed line and to a retrograde cardioplegia catheter having a pressure sensing feed line, the system comprising:

(a) a stopcock comprising:
 (i) a hollow valve body comprising;
  (A) a first cylindrical shell;
  (B) a second cylindrical shell disposed coaxially with said first cylindrical shell at a first end thereof; and
  (C) a sleeve encircling said first end of said first cylindrical shell and the end of said second cylindrical shell opposed thereto to maintain a fixed spacial relationship between said first and said second cylindrical shells;
 (ii) first, second, and third cardioplegia solution infusion ports communicating through the walls of said first cylindrical shell to the interior thereof;
 (iii) first, second, and third cardioplegia pressure monitoring ports communicating through the walls of said second cylindrical shell to the interior thereof; and
 (iv) a cylindrical valve core mounted in said valve body for selective rotation about the longitudinal axis thereof between a first position in which a first and a second of said infusion ports and a first and a second of said pressure monitoring ports are placed in fluid communication, and a second position in which said second and a third of said infusion ports and said second and a third of said pressure monitoring ports are placed in fluid communication;

(b) first pressure tubing secured to said first pressure monitoring port for placing said first pressure monitoring port in communication with the pressure sensing feed line of the antegrade cardioplegia catheter;

(c) second pressure tubing secured to said second pressure monitoring port for placing said second pressure monitoring port in communication with the pressure monitor;

(d) third pressure tubing secured to said third pressure monitoring port for placing said third pressure monitoring port in communication with the pressure sensing feed line of the retrograde cardioplegia cannula;

(e) first infusion tubing secured to said first infusion port for placing said first infusion port in fluid communication with said antegrade cardioplegia catheter;

(f) second infusion tubing secured to said second infusion port for placing said second infusion port in fluid communication with the source of cardioplegia solution;

(g) third infusion tubing secured to said third solution infusion port for placing said third infusion port in fluid communication with said retrograde cardioplegia cannula; and (h) actuation means for selectively moving said cylindrical valve core between said first and said second positions thereof to alternately perform antegrade and retrograde cardioplegia procedures using the pressure monitor the and source of cardioplegia solution.

30. A system as recited in claim 29, wherein formed in said cylindrical core are:
   (a) a first set of valving passageways for communicating with selective of said infusion ports; and
   (b) a second set of valving passageways for communicating with selective of said pressure monitoring ports.

31. A system as recited in claim 29, wherein said infusion ports are radially disposed in a coplanar configuration at a first longitudinal position on said valve body; and wherein said pressure monitoring ports are radially disposed in a coplanar configuration at a second longitudinal position on said valve body distinct from said first longitudinal position.

32. A system as recited in claim 31, wherein said first, second, and third infusion ports communicate with the exterior of said valve body through radially extending first, second, and third infusion connection stems, respectively; and wherein said first, second, and third pressure monitoring ports communicate with the exterior of said valve body through radially extending first, second, and third pressure monitoring connection stems, respectively.

33. A system as recited in claim 32, wherein said first, second, and third infusion connection stems are longitudinally aligned on the sides of said valve body with said first, second, and third pressure monitoring stems, respectively; and wherein said first infusion and pressure monitoring connection stems are located on diametrically opposite sides of said valve body from said third fluid and pressure monitoring connection stems and said second infusion and pressure monitoring connection stems are spaced at right angles about said valve body from said first and said third infusion and pressure monitoring connection stems.

34. A system as recited in claim 29, wherein the ends of said pressure tubing and said infusion tubing remote from said stopcock are provided with a fitting for effecting a fluid-tight coupling.

35. A system as defined in claim 29, wherein said pressure monitoring tubing and said infusion tubing are permanently secured to said stopcock.

36. A system as recited in claim 29, wherein the length of said first pressure monitoring tubing and said first infusion tubing is in the range of about 10.0 to about 15.0 inches.

37. A system as recited in claim 29, wherein the length of said first pressure monitoring tubing and said first infusion tubing is in the range of about 70.0 inches to about 95.0 inches.

38. A system as recited in claim 29, wherein the length of said third pressure monitoring tubing and said third infusion tubing is in the range of about 4.0 inches to about 10.0 inches.

39. A system as recited in claim 29, wherein the length of said third pressure monitoring tubing and said third infusion tubing is in the range of about 64.0 inches to about 90.0 inches.

40. A system as recited in claim 29, wherein the length of said second pressure monitoring tubing is in the range of about 60.0 inches to about 80.0 inches.

41. A system as recited in claim 29, wherein the length of said second infusion tubing is the range of about 3.0 inches to about 8.0 inches.

42. A method for conducting a cardioplegia procedure comprising the steps of:
   (a) installing in a patient an antigrade cardioplegia cannula having a pressure sensing feed line;
   (b) installing in a patient a retrograde cardioplegia catheter having a pressure sensing feed line;
   (c) providing a three-way double stopcock, said stopcock comprising:
      (i) a hollow valve body;
      (ii) first, second, and third cardioplegia solution infusion ports communicating through the walls of said valve body to the interior thereof;
      (iii) first, second, and third cardioplegia pressure monitoring ports communicating through the walls of said valve body to the interior thereof;
      (iv) a cylindrical valve core mounted in said valve body for selective rotation about the longitudinal axis thereof between a first position in which a first and a second of said infusion ports and a first and a second of said pressure monitoring ports are placed in fluid communication, and a second position in which said second and a third of said infusion ports and said second and a third of said pressure monitoring ports are placed in fluid communication; and
      (v) actuation means for selectively moving said cylindrical valve core between said first and second positions thereof to alternatively perform antigrade and retrograde cardioplegia procedures using the pressure monitor and the source of cardioplegia solution;
   (d) placing said first pressure monitoring port in communication with the pressure sensing feed line of the antigrade cardioplegia catheter;
   (e) placing said second pressure monitoring port in communication with a pressure monitor;
   (f) placing said third pressure monitoring port in communication with the pressure sensing feed line of the retrograde cardioplegia cannula;
   (g) placing said first infusion port in fluid communication with said antigrade cardioplegia catheter;
   (h) placing said second infusion port in fluid communication with a source of cardioplegia solution;
   (i) placing said third infusion port in fluid communication with said retrograde cardioplegia cannula; and
   (j) alternately operating said actuation means to move said cylindrical valve core between said first and second positions thereof.

* * * * *

UNITED STATES PATENT AND TRADEMARK OFFICE
CERTIFICATE OF CORRECTION

PATENT NO. : 5,084,031

DATED : January 28, 1992

INVENTOR(S) : ROBERT J. TODD et al.

It is certified that error appears in the above-identified patent and that said Letters Patent is hereby corrected as shown below:

On the title page,
    Abstract, line 19, "are" should be --is--
    Column 1, line 47, "flow through" should be --flowthrough--
    Column 2, line 5, "flow through" should be --flowthrough--
    Column 2, line 24, after "thus" insert --be--
    Column 2, line 43, after "and in" insert --the pressure monitoring tubing to one side of the heart being--
    Column 3, line 62, after "placed" insert --in fluid communication. In the second condition, the second--
    Column 4, line 13, after "port" insert --are--
    Column 4, line 22, "cardioplegia" should be --cardioplegic--
    Column 5, line 6, "spacial" should be --spatial--
    Column 5, line 25, after "drawings" insert --.--
    Column 5, lines 25-26, "there drawings" should be --these drawings--
    Column 7, line 2, after "inches" insert --.--
    Column 10, line 48, delete first occurrence of "be"
    Column 12, line 18, "spacial" should be --spatial--
    Column 12, line 57, after "axially" insert --beyond said valve body, and said one end is provided with an--
    Column 13, line 55, "spacial" should be --spatial--
    Column 14, line 8, "spacial" should be --spatial--

UNITED STATES PATENT AND TRADEMARK OFFICE
CERTIFICATE OF CORRECTION

PATENT NO. : 5,084,031

DATED : January 28, 1992

INVENTOR(S) : ROBERT J. TODD et al.

It is certified that error appears in the above-identified patent and that said Letters Patent is hereby corrected as shown below:

```
Column 15, line 52, "spacial" should be --spatial--
Column 16, line 16, "spacial" should be --spatial--
Column 16, line 68, "the and source" should be --with the source--
Column 18, line 11, "antigrade" should be --antegrade--
Column 18, line 37, "antigrade" should be --antegrade--
Column 18, line 42, "antigrade" should be --antegrade--
Column 18, line 49, "antigrade" should be --antegrade--
```

Signed and Sealed this

Twenty-eighth Day of December, 1993

*Attest:*

BRUCE LEHMAN

*Attesting Officer*    *Commissioner of Patents and Trademarks*